(12) United States Patent
Schwobel et al.

(10) Patent No.: US 6,207,000 B1
(45) Date of Patent: Mar. 27, 2001

(54) PROCESS FOR THE PRODUCTION OF ANALYTICAL DEVICES

(75) Inventors: Wolfgang Schwobel, Mannheim; Bernd Hein, Dossenheim, both of (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/283,996

(22) Filed: Apr. 1, 1999

(30) Foreign Application Priority Data

Apr. 8, 1998 (DE) .............................................. 198 15 684

(51) Int. Cl.⁷ .......................... B32B 31/00; G01N 33/48
(52) U.S. Cl. ...................... 156/248; 156/257; 156/254; 156/268; 156/269; 156/270; 422/58; 422/59; 422/60
(58) Field of Search .................................. 156/248, 257, 156/64, 254, 267, 268, 269, 270; 422/58, 59, 60

(56) References Cited

U.S. PATENT DOCUMENTS

| | | | |
|---|---|---|---|
| 4,761,381 | * | 8/1988 | Blatt et al. .......................... 436/165 |
| 5,120,420 | * | 6/1992 | Nankai et al. ....................... 204/403 |
| 5,248,479 | * | 9/1993 | Parsons et al. ........................ 422/58 |
| 5,437,999 | * | 8/1995 | Diebold et al. ....................... 435/288 |
| 5,798,031 | * | 8/1998 | Charlton et al. ...................... 204/403 |
| 5,997,817 | * | 12/1999 | Crismore et al. ....................... 422/58 |

FOREIGN PATENT DOCUMENTS

| | | |
|---|---|---|
| 196 29 656 A1 | 7/1996 | (DE) . |
| 0 138 152 B1 | 4/1985 | (EP) . |
| 0 212 314 | 3/1987 | (EP) . |
| 0 287 883 | 10/1988 | (EP) . |

* cited by examiner

Primary Examiner—Linda L. Gray
(74) Attorney, Agent, or Firm—Brent A. Harris; Roche Diagnostics Corporation

(57) ABSTRACT

A process for the production of analytical devices is provided in accordance with the present invention. Analytical devices include analytical test elements with a capillary-active zone for examining liquid samples. In the process a carrier layer is prepared, a spacer layer is laminated onto the carrier layer, a contour is punched, cut or stamped through the spacer layer laminated onto the carrier layer which determines the shape of the capillary-active zone, those parts of the spacer layer which are not required to form the capillary-active zone are removed from the carrier layer and a cover layer is applied to the spacer layer to result in a capillary-active zone. The process according to the invention is preferably suitable for manufacturing analytical devices from tape material.

22 Claims, 3 Drawing Sheets

PROCESS FOR THE PRODUCTION OF ANALYTICAL DEVICES

FIELD OF THE INVENTION

The invention concerns a process for the production of analytical devices with a capillary-active zone, preferably of analytical test elements for examining liquid samples. In particular the invention concerns a process for the production of analytical devices from tape material. In addition the invention concerns analytical devices which have been produced by the process according to the invention.

BACKGROUND AND SUMMARY OF THE INVENTION

So-called carrier-bound tests (test carriers, test elements) are often used for the qualitative or quantitative analytical determination of components of liquid samples e.g. body fluids such as blood, serum or urine. In these tests the reagents are embedded in corresponding layers of a solid carrier which is contacted with the liquid sample. If a target analyte is present, the reaction of the liquid sample and reagents leads to a detectable signal, which is usually a colour transition, which can be evaluated visually or with the aid of an instrument e.g. by reflection photometry.

Test elements or test carriers are often in the form of test strips which are essentially composed of an elongate support layer made of plastic material and detection layers as test zones that are attached thereto. However, test carriers are also known which are designed as quadratic wafers.

Test elements for clinical diagnostics that are evaluated visually or by reflection photometry are frequently constructed such that the sample application zone and the detection zone are arranged above one another in a vertical axis so that for example the sample is applied from above onto a sample application zone and a change of colour is observed from below. This mode of construction is problematic. When the test strip loaded with sample has to be inserted into an instrument for example a reflection photometer, for measurement, potentially infectious sample material can come into contact with parts of the instrument and may contaminate them. Furthermore volumetric dosing can only be achieved with difficulty especially in cases in which the test strips are used by untrained persons for example in the self-control of blood sugar by diabetics. Moreover conventional test elements often require relatively large sample volumes due to their construction in order to enable reliable measurements. The more sample volume is required, the more painful the sample collection may be for the patient whose blood is to be examined. The goal is therefore to provide test strips which require as little sample material as possible.

The use of analytical test elements with capillary-active zones is one method of reliably dosing small amounts, typically a few microlitres, of sample volume and transporting it within the test element. Such test elements are described in the prior art.

EP-B 0 138 152 concerns a disposable cuvette which is suitable for almost simultaneously taking up sample liquid into a sample chamber with the aid of a capillary gap and measuring it. Reagents can be provided inside the void space of the capillary. The void space is at least partially bordered by a semi-permeable membrane. The reagents can for example be accommodated in the void space by coating the walls or by embedding the reagents in a semi-permeable membrane.

EP-A-0 287 883 describes a test element which utilizes a capillary interstitial space between a detection layer and an inert carrier for the volumetric dosing. In order to fill the capillary space, the test element is dipped into the sample to be examined which requires large sample volumes and is why this type of volumetric dosing is preferably used for examining sample material that is present in excess such as urine.

An analytical test element with a capillary-active zone is also known from EP-A 0 12 314. In order to manufacture this test element it is proposed that an intermediate layer which contains a cut-out corresponding to the capillary-active zone is placed between two plastic layers. According to EP-A 0 212 314 the cut-out should already be present in the intermediate layer before assembly. Especially when using flexible intermediate layers such as for example double-sided adhesive tapes, it is difficult to assemble the analytical element since an exact, reproducible positioning of the intermediate layer which already contains a cut-out is difficult and complicated to accomplish.

The object of the invention is to eliminate the disadvantages of the prior art. In particular the object of the present invention is to provide a process with which analytical devices can be produced cheaply, reproducibly and exactly.

The subject of the invention is a process for the production of analytical devices with a capillary-active zone in which (a) a carrier layer is prepared;
(b) a spacer layer is laminated onto the carrier layer;
(c) a contour which determines the shape of the capillary-active zone is punched, cut or stamped through the spacer layer laminated onto the carrier layer;
(d) those parts of the spacer layer are removed from the carrier layer which are not required for shaping the capillary-active zone; and
(e) a cover layer is placed on the spacer layer so that a capillary-active zone is formed as well as analytical devices produced accordingly.

Analytical devices in the sense of the invention are understood as devices which can automatically take up sample liquids with the aid of their capillary-active zone, i.e. by capillary forces, and can make them available for a simultaneous or later analysis. The capillary-active zone can be present as a capillary gap or can be generated by using capillary-active porous materials such as e.g. fleeces, papers or membranes.

Analytical devices can preferably be analytical test elements in which suitable detection reactions which allow the determination of the presence or amount of an analyte in the sample proceed already during or after the uptake of sample liquid. However, analytical devices in the inventive sense can also be cuvettes or pipettes which only utilize the sample pick-up by the capillary zone and in which the sample is either released again for the analysis or in which the analysis occurs without subsequent reactions. The analytical devices can of course also be used to store and keep sample liquids.

The presence of a capillary-active zone in the analytical devices produced according to the invention enables an automatic uptake of a defined sample volume if the capillary-active zone is manufactured accurately and reproducibly enough. The capillary-active zone can have any desired shape provided capillarity is ensured in at least one dimension. The capillary-active zone can for example have a triangular, rectangular or semi-circular ground plan and the corners of the outlined areas are preferably rounded as a precaution against the risk of remnants of adhesive in the capillary-active zone. Capillary-active zones are preferred according to the invention with an essentially cuboid geometry i.e. with an essentially rectangular ground plan.

Many materials that are conventionally used to manufacture analytical devices can be employed as the carrier layer to produce an analytical device according to the invention such as test elements e.g. metal or plastic foils, coated papers or cardboards and, although less preferred, glass. If the analytical device is used to examine nonpolar liquids, an adequate capillarity of the capillary zone of the analytical device produced according to the invention is already achieved by using nonpolar carrier layers e.g. plastic foils. In order to achieve an adequate capillarity when examining aqueous samples such as e.g. water samples or biological liquids such as blood, serum, urine, saliva or sweat, it is advantageous if the carrier material that is used has a hydrophilic surface on at least the side facing the capillary-active zone.

In this connection hydrophilic surfaces are water-attracting surfaces. Aqueous samples, also including blood, spread well on such surfaces. Such surfaces are characterized among others in that a water drop placed on it forms an acute rim angle or contact angle at the interface (cf. for example details under the heading "Benetzung" in "CD Römpp Chemie Lexikon", Version 1.0, 1995). In contrast an obtuse rim angle is formed at the interface between a water drop and surface on hydrophobic i.e. water repellent surfaces.

The rim angle which is a result of the surface tensions of the test liquid and of the surface to be examined is a measure of the hydrophilicity of a surface. Water for example has a surface tension of 72 mN/m. If the value of the surface tension of the observed surface is much below this value i.e. more than 20 mN/m below this value, then the wetting is poor and the resulting rim angle is obtuse. Such a surface is referred to as hydrophobic. If the surface tension approximates the value which is found for water then the wetting is good and the rim angle is acute. If, in contrast, the surface tension is the same as or higher than that of the value found for water, then the drop runs and there is a total spreading of the liquid. It is then no longer possible to measure a rim angle. Surfaces which form an acute rim angle with water drops or on which a total spreading of a water drop is observed, are referred to as hydrophilic.

The ability of a capillary to aspirate a liquid depends on the wettability of the capillary surface with the liquid. This means for aqueous samples that a capillary should be manufactured from a material whose surface tension almost reaches 72 mN/m or exceeds this value.

Sufficiently hydrophilic materials for the construction of a capillary which rapidly aspirates aqueous samples are for example glass, metal or ceramics. However, these materials are often unsuitable for use in analytical devices such as test carriers since they have some disadvantages such as risk of breaking in the case of glass or ceramics or change in the surface properties with time in the case of numerous metals. Therefore plastic foils or moulded parts are usually used to manufacture analytical devices. As a rule the plastics used hardly exceed a surface tension of 45 mN/m. Even with the, in a relative sense, most hydrophilic plastics such as polymethylmethacrylate (PMMA) or polyamide (PA) it is only possible—if at all—to construct capillaries that aspirate very slowly. Capillaries made of hydrophobic plastics such as for example polystyrene (PS), polypropylene (PP) or polyethylene (PE) essentially do not aspirate aqueous samples. Consequently it is necessary to endow the plastics used as a construction material for analytical devices with a capillary-active zone, such as e.g. test elements with a capillary gap, with hydrophilic properties i.e. to hydrophilize them.

In a preferred embodiment of the analytical devices produced according to the invention at least one, but preferably two and especially preferably two opposite surfaces which form the inner surface of the channel capable of capillary liquid transport, are hydrophilized. If more than one surface is hydrophilized then the surfaces can either be made hydrophilic using the same or different methods. Hydrophilization is particularly necessary when the materials that form the capillary-active channel, in particular the carrier layer, are themselves hydrophobic or only very slightly hydrophilic because they are for example composed of nonpolar plastics. Nonpolar plastics such as for example polystyrene (PS), polyethylene (PE), polyethylene terephthalate (PET) or polyvinyl chloride (PVC) are advantageous as carrier materials because they do not absorb and are not attacked by the aqueous liquids to be examined. The hydrophilization of the surface of the capillary zone enables a polar, preferably aqueous, sample liquid to readily enter the capillary-active zone. If the analytical device is a test element, the aqueous sample is additionally rapidly transported to the detection element or to the site of the detection element where the detection takes place.

Ideally the hydrophilization of the surface of the capillary-active zone is achieved by using a hydrophilic material in its manufacture which, however, cannot itself absorb the sample liquid or only to a negligible extent. In cases where this is not possible a hydrophobic or only very slightly hydrophilic surface can be hydrophilized by suitable coating with a stable hydrophilic layer that is inert towards the sample material, for example by covalently binding photoreactive hydrophilic polymers onto a plastic surface by applying layers containing wetting agents or by coating surfaces with nanocomposites by means of sol-gel technology. Furthermore, it is also possible to increase the hydrophilicity by thermal, physical or chemical treatment of the surface.

The hydrophilization is quite especially preferably achieved by using thin layers of oxidized aluminium as described in the German Patent Application No. P19753848.7. These layers are either applied directly to the desired components of the test element, for example by vacuum coating the work pieces with metallic aluminium and subsequently oxidizing the metal, or by using metal foils or metal-coated plastiOs for the construction of the test carriers which also have to be oxidized to achieve the desired hydrophilicity. In this case metal layer thicknesses of 1 to 500 nm are adequate. The metal layer is subsequently oxidized to form the oxidized form in which case above all oxidation in the presence of water vapour or by boiling in water have proven to be especially suitable methods in addition to electrochemical, anodic oxidation. The oxide layers formed in this manner are between 0.1 and 500 nm, preferably between 10 and 100 nm thick depending on the method. Larger layer thicknesses of the metal layer as well as of the oxide layer can in principle be achieved in practice but do not exhibit any additional advantageous effects.

The capillary zone of the analytical device produced according to the invention is formed from the carrier layer, a spacer layer and a cover layer. The purpose of the spacer layer is preferably to define the dimension which results in the capillarity of the zone. The thickness of the spacer layer is preferably used to define this dimension. However, it is also possible to cut out or punch out a piece of appropriate width from the spacer layer resulting in a zone of a capillary-active dimension. At least one dimension of the zone is defined by the physical limits of capillary activity. In the case of aqueous liquids this dimension is of the order of magnitude of 10 to 500 $\mu$m, preferably between 20 and 300 $\mu$m and most preferably between 50 and 200 $\mu$m since otherwise no capillary activity would be observed.

Although the spacer layer can in principle be manufactured from all materials that are inert towards the sample liquid to be analysed, double-sided adhesive tape has proven to be preferable since this simply solves the problem of attaching the spacer layer on the carrier layer on the one hand and of the cover layer on the other hand. This avoids time consuming and costly bonding or adhesive processes in the manufacture of the analytical device. However, if this advantage is not utilized, the analytical device can also be produced according to the invention using additional bonding processes e.g. by welding, heat-sealing for example with polyethylene, glueing with cold-setting adhesive or hot-melt adhesive, or by clipping the carrier layer to a spacer layer or the spacer layer to the cover layer. In this connection the spacer layer can in principle be manufactured from the materials which are also suitable for the carrier layer.

Since the spacer layer together with the carrier layer and the cover layer determines the geometry of the capillary-active zone, a contour is introduced into the spacer layer in the process according to the invention after the spacer layer has been mounted on the carrier layer which allows those parts of the spacer layer that are not required to form the geometry of the capillary-active zone to be removed again from the carrier layer. An example is that part of the spacer layer which forms the capillary region of the analytical device after detachment from the carrier layer.

The contour can in principle be introduced by the spacer layer using all methods which enable a clean separation of the parts of the spacer layer that remain on the carrier layer from those parts that are to be removed from the carrier layer. Examples are punching, cutting or stamping, of which punching or cutting are preferred according to the invention. It has turned out to be particularly advantageous for a clean separation of the parts of the spacer layer remaining on the carrier layer from the parts that are to be removed from the carrier layer, if the contour is cut through the spacer layer and thus slightly cuts into the carrier layer, care being taken that the cut in the carrier layer is not deep enough to make it unstable. This can be reliably avoided by suitably precise cutting tools.

For the preferred embodiment of the analytical device in which the spacer layer is formed from a double-sided adhesive tape, it has turned out to be advantageous to laminate the spacer layer on the carrier layer immediately before punching, cutting or stamping the contour of the capillary-active zone and to remove those parts of the spacer layer that are not required to form the capillary-active zone immediately after punching, cutting or stamping the contour of the capillary-active zone. When the said parts are removed this avoids problems such as e.g. adhesive residues remaining in the capillary-active zone or bonding of the parts of the spacer layer separated by punching, cutting or stamping. In addition it was surprisingly found that the edges of the cut out area in the spacer layer are particularly smooth compared to using pre-punched adhesive tapes and are thus favourable for the capillarity.

With the preferred use of double-sided adhesive tape as the spacer layer it is necessary, after removing the parts of the adhesive tape that are not required and before applying the cover layer, to remove the cover foil (interliner) of the adhesive tape that is generally present to enable bonding of the cover layer.

All materials that are also suitable for the carrier layer are suitable as the cover layer for the capillary-active zone of the analytical device produced according to the invention. Consequently the analytical device can be essentially composed of identical materials for the carrier layer, spacer layer and cover layer, but any combinations of materials are also possible. For the preferred case in which the analytical device is used for an optical examination of the sample material, it is advantageous if at least carrier layer or the cover layer or both are completely or partially manufactured from a transparent material, preferably a transparent plastic.

For the preferred case that the process according to the invention is used to produce an analytical test element, a one-piece layer is used as the carrier layer whereas the cover layer can be composed of one or several parts. The cover layer can be completely or partially composed of an analytical detection film as described for example in the German Patent Application No. P 196 29 656.0.

This detection film is composed of two film layers on a transparent foil and the film as a whole contains all reagents and auxiliary substances that are required for an analytical detection reaction with the sample liquid. Such reagents and auxiliary substances are known to a person skilled in the art in numerous variants for numerous analytes for example from the German Patent Application No. P 196 29 656.0. The reagents and auxiliary substances contained in the detection film preferably lead to a qualitative or quantitative signal that can be detected visually or optically by means of an apparatus when the target analyte is present in the liquid sample to be examined.

An important feature of the detection film that is preferred here for the preferred embodiment of an analytical test element is that the first layer lying on the transparent foil scatters light considerably less than the overlying second layer. Whereas the first layer contains a swelling agent such as methylvinyl-ether-maleic acid copolymer and optionally a weakly light-scattering filler, the second layer requires a swelling agent and in any case at least one strongly light-scattering pigment and can also additionally contain non-porous fillers and porous fillers such as kieselguhr in small amounts without becoming permeable for particulate sample components such as erythrocytes.

Since the weakly light-scattering fillers and the strongly light-scattering pigments are essentially responsible for the optical properties of the film layers, the first and the second film layer contain different fillers and pigments. The first film layer should either contain no fillers or fillers whose refractive index is close to the refractive index of water for example silicon dioxide, silicates and aluminium silicates. The average particle size of particularly preferred filler particles is about 0.06 $\mu$m. The second layer should advantageously be very strongly light-scattering. The refractive index of the pigments of the second film layer is ideally at least 2.5. Hence titanium dioxide is preferably used. Particles with an average diameter of about 0.2 to 0.8 $\mu$m have proven to be particularly advantageous.

Furthermore it has proven to be preferable that, when using a detection film, the cover layer is additionally formed by an additional cover foil which preferably lies next to the detection film and, like this, is on the side of the carrier layer that is opposite to the capillary zone. The cover foil replaces the detection element on part of the capillary zone. Since the detection element usually contains valuable reagents such as enzymes and, due to its often complex structure, is much more expensive to manufacture than a simple cover foil, this measure considerably reduces the material and production costs. This applies particularly to the case of long capillary zones which are understood as zones of more than 5 mm in length. Moreover in test elements in which the detection reaction is detected in the detection film in a spatially exactly defined region, for example in the case of optical detection in an instrument, and in which it is desirable to separate the sample application zone and detection zone, for example for reasons of instrument hygiene, this measure enables an accelerated sample transport from the sample application opening in the test element to the detection site in the detection element so that the transport of the sample in the capillary channel from the sample application zone to the detection area is so rapid that it does not impose any time limitations on the analysis of a sample. In addition such an arrangement makes it more convenient to use for the user.

The cover foil and detection film must be assembled such that they abut each other in the final test element so that the liquid transport is not interrupted in the capillary at the site of contact of the cover foil and detection film by for example an unfavourable change in the capillary cross-section which is also understood to include an interruption of a continuous boundary surface of the capillary. For this purpose the dimensions of the detection film and cover foil should be matched appropriately. If it is not possible to assemble the two components close enough together, an interruption of the capillary-active zone can be avoided by subsequent sealing.

Surprisingly it was found that for a particularly preferred embodiment of the test element produced according to the invention a flexible inert foil can additionally be mounted on the side of the cover foil facing the channel capable of capillary liquid transport, which extends over the entire length of the cover, covers the capillary zone over its entire width and is at least partially enclosed between the opposed edge surfaces of the cover foil and detection film so that the capillary liquid transport does not break down at the contact site of the detection film and cover foil. The material and optionally the hydrophilizing coating of the foil can essentially correspond to that already described above for the carrier layer and cover layer. In this especially preferred variant the detection film and cover foil are also mounted as closely together as possible.

The process according to the invention is preferably used to produce analytical devices in large numbers so that the process can be substantially automated. For this purpose the materials for the analytical devices such as the carrier layer, the spacer layer and the cover layer are provided in the form of tape material similar to a roll of film. The contour which determines the shape of the capillary-active zone is preferably cut through the spacer layer which is laminated onto the carrier layer by using a rotating cutting tool which preferably contains a cutting roller and a counter-pressure cylinder. This advantageously results in a continuous cut in or through the spacer layer which has a precise and reproducible relative position on the continuous tape and consequently on the analytical devices manufactured according to the invention.

In this particularly preferred process according to the invention the analytical devices, for example the analytical test elements, are separated after mounting the cover layer by cutting or punching i.e. separated from the previous tape form as preferably narrow, essentially rectangular strips. Hence the production according to the invention can be carried out in one operation at a high production rate (0.1 m/min to ca. 50 m/min).

The advantages of the invention can be summarized as follows:

♦ An extensive automation of the production process is possible and hence the production costs for the individual analytical devices remain low.

♦ The position and size of the capillary-active zone on the analytical device are accurately and reproducibly maintained; its position relative to other functional components of the analytical device can be readily adjusted and is reproducible.

♦ The capillary-active zone has exact and cleanly defined borders with the spacer layer which enables the capillary properties to be precisely adjusted.

BRIEF DESCRIPTION OF THE DRAWINGS

The invention is further elucidated by the following examples and figures.

DETAILED DESCRIPTION OF THE INVENTION

Figure 1:
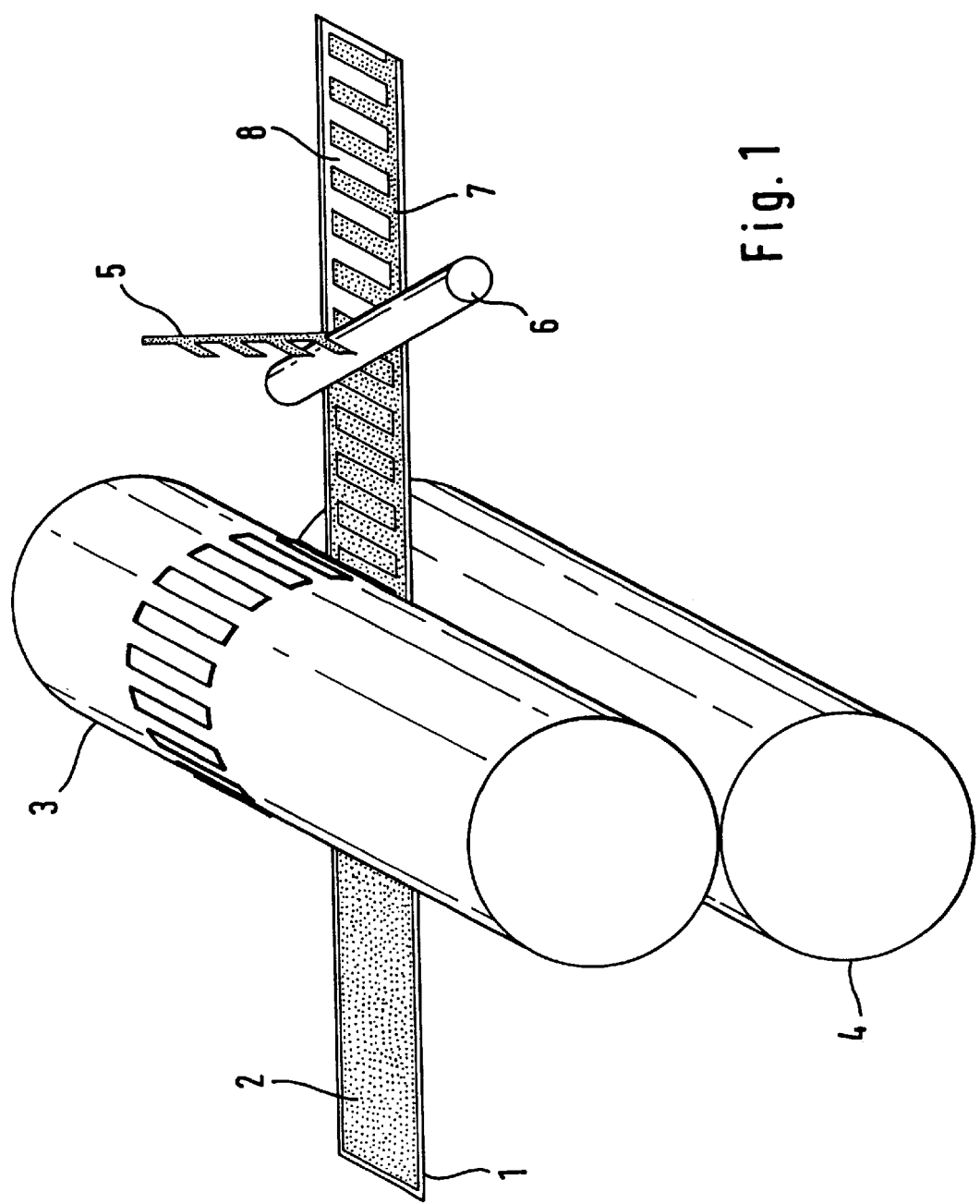
FIG. 1 shows schematically a part of the automatic manufacture of an analytical device according to a preferred embodiment of the process according to the invention.

The numbers in the figures denote:
1 carrier layer
2 spacer layer (spacer)
3 cutting roller
4 counterpressure cylinder
5 remainder of the spacer layer that has to be pulled off the carrier layer
6 withdrawal roller
7 remnant of the spacer layer remaining on the carrier layer
8 capillary-active zone
9 recess in the carrier layer
10 detection film
11 cover foil
12 protective foil Part of an automatic production plant for analytical devices and in particular for analytical test elements is shown schematically in FIG. 1 which operates according to a particularly preferred variant of the process according to the invention. In FIG. 1 a carrier layer 1 on which a spacer layer 2 has already been laminated in the form of a double-sided adhesive tape in an immediately preceding production step, is made available as tape material on the left and is automatically transported to the right. In this process the laminate composed of carrier layer 1 and spacer layer 2 passes through a rotary cutting tool containing a cutting roller 3 and a counterpressure cylinder 4 which introduce a contour in the shape of an essentially rectangular meander through the spacer layer 2 using the cutting roller 3 which determines the geometry of the capillary-active zone of the final analytical test element. Immediately after passing the cutting tool containing a cutting roller 3 and a counterpressure cylinder 4, the remainder 5 of the spacer layer 2 that is to be removed is pulled off the carrier layer 1. The withdrawal roller 6 which is passed through in this process ensures that the part 5 of the spacer layer 2 that is to be pulled off is pulled off cleanly and free of remnants in the direction of the cut capillary geometry without the remainder 5 tearing during the stripping. Very narrow remnants 5 of the spacer layer 2 can be reproducibly and reliably removed in this manner. The remnant 7 of the spacer layer 2 that remains on the carrier layer essentially determines the geometry of the capillary-active zone 8 which is formed by subsequent covering of the spacer layer 2 with a cover foil which is not shown in this figure, during which the interliner of the adhesive tape is removed immediately before mounting the cover foil. Individual test elements which each have a capillary-active zone 8 are obtained at the end of the manufacturing process from the continuous tape generated in this manner composed of carrier layer 1, spacer layer 2 and a cover foil by cutting or punching.

Figure 2:
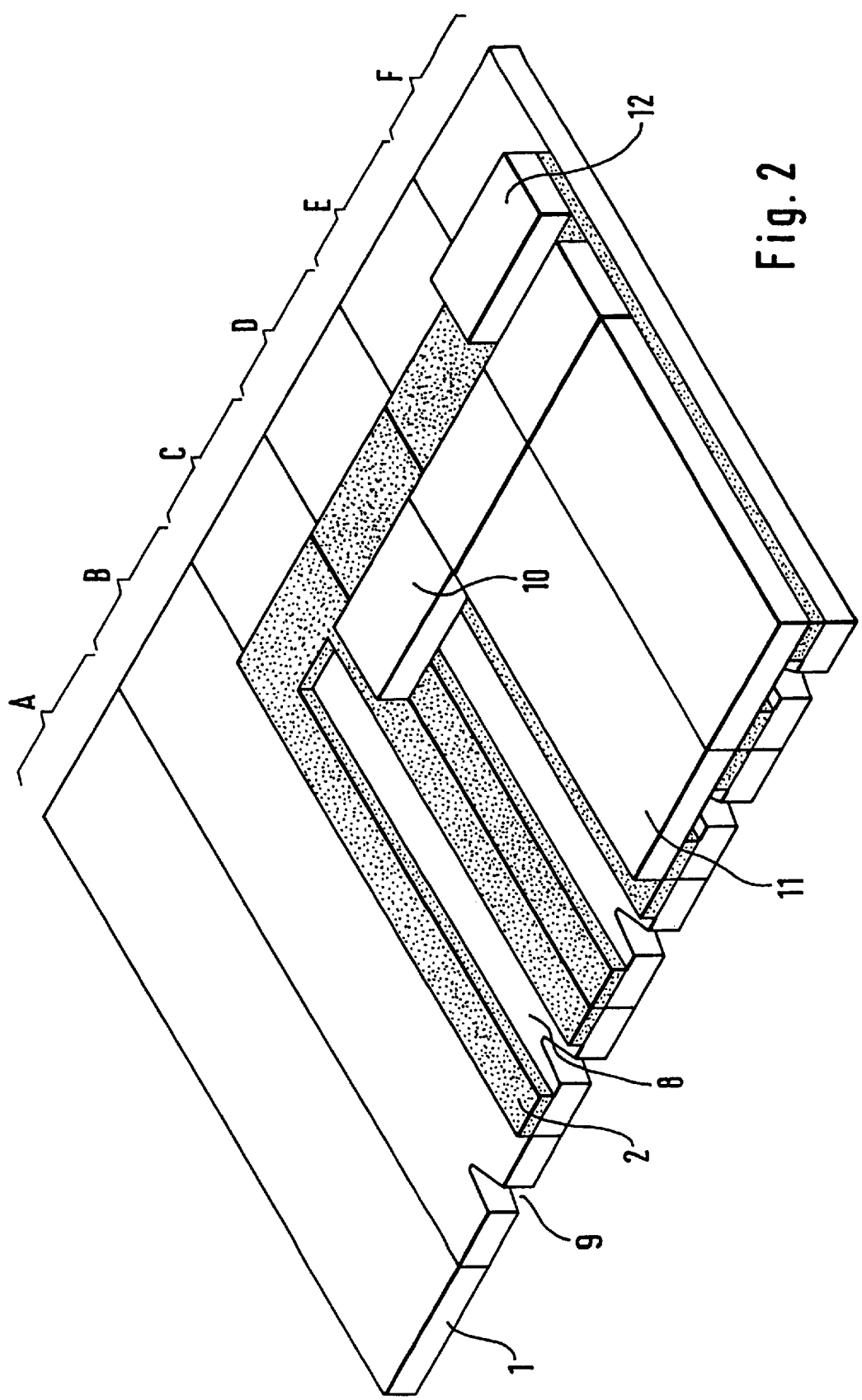
FIG. 2 shows schematically six stages (A to F) of the manufacture of an analytical device according to a preferred embodiment of the process according to the invention.

Six manufacturing stages (A to F) of the analytical test element that can be produced according to a preferred embodiment of the invention are shown schematically in FIG. 2. In stage A a carrier layer 1 is prepared in which a notch 9 is punched which in the final analytical test element can serve among others as an orientation aid for sample application and to facilitate sample uptake into the capillary (stage B). Stage C shows the carrier layer 1 on which, after introducing the notch 9, a spacer layer 2 has been applied in the form of a double-sided adhesive tape. In this case the contour of the capillary zone 8 has already been cut through the spacer layer 2, the non-required remnants of the spacer layer 2 have been stripped off and the cover foil (interliner) has been pulled off the adhesive tape. Subsequently (stage D) an analytical detection film 10 is laminated onto the appropriate site of the spacer layer 2 remaining on the carrier layer 1. The remaining, previously uncovered area of the capillary-active zone 8 is covered with a cover foil to result in a continuous capillary-active zone which includes the cover foil 11 as well as the detection film 10 (stage E). For manufacturing reasons remaining exposed areas of adhesive tape are subsequently provided with a protective foil 12 which is intended to prevent an undesired adhesion of analytical test elements manufactured according to the invention (stage F). Hence a small gap usually of a few millimeters in size usually remains in this process between the protective foil 12 and detection film 10 which allows air to escape from the capillary-active zone when it is filled with sample liquid. For the same reason zone 8 is not completely covered by the cover foil 11 and the detection element 10 is not completely covered on the side facing the protective foil 12.

Figure 3:
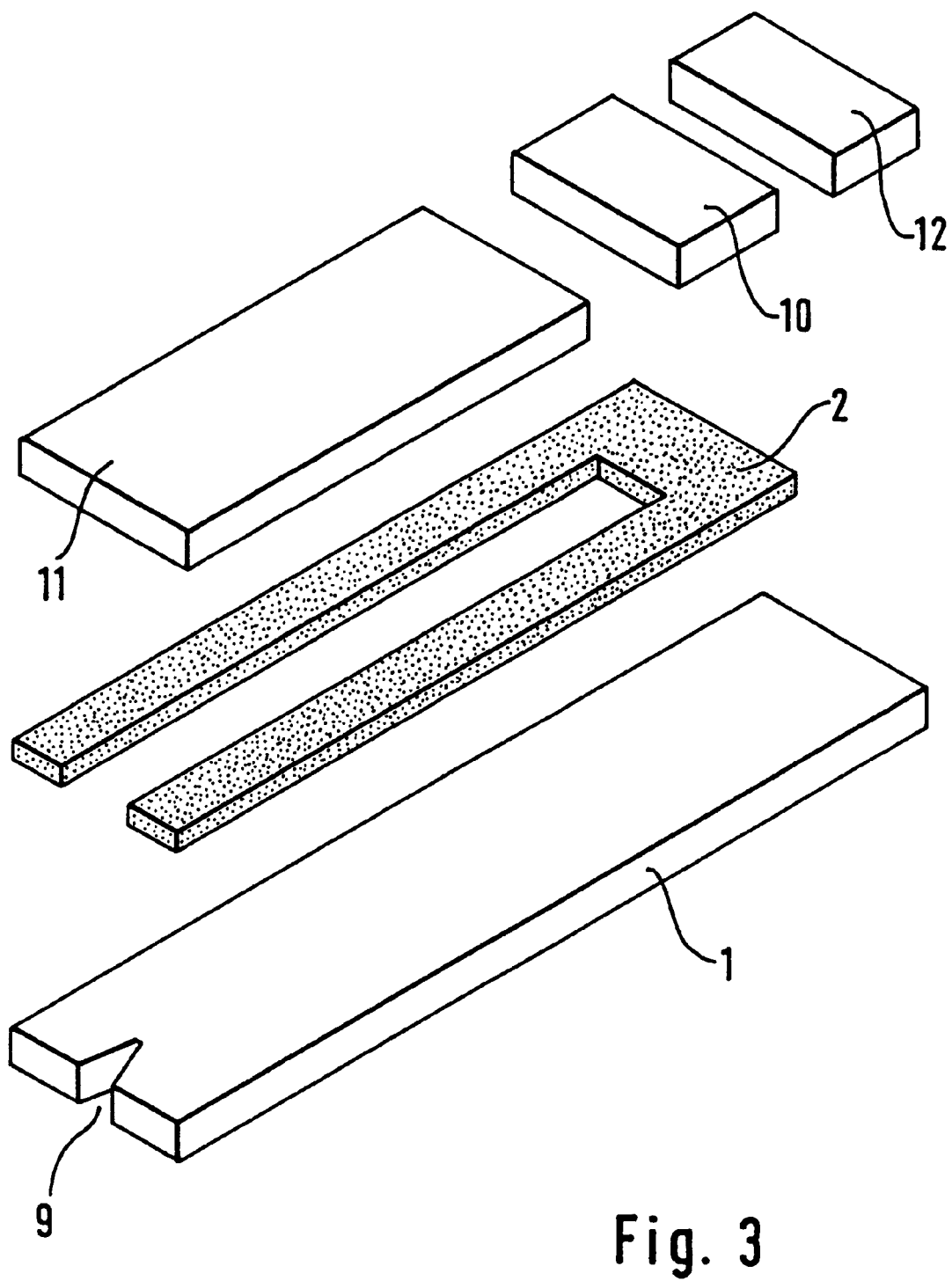
FIG. 3 shows a schematic exploded diagram of a preferred embodiment of an analytical device which can be produced by the process according to the invention.

The analytical test element of FIG. 2 produced according to the invention is again shown schematically in FIG. 3 in an exploded diagram. A spacer layer 2 which defines the contour and the height (corresponding to the thickness of the spacer layer) of the capillary-active channel is located on the carrier layer 1 in which a notch 9 has been introduced. A cover foil 11, a detection film 10 as well as a protective foil 12 are in turn placed on this. The cover foil 11 and detection film 10 are mounted so closely together that the capillary-active zone extends from the free edge of the cover foil 11 lying over the notch 9 up to the opposite free edge of the detection film 10. The cut-out area in the spacer layer 2 is made slightly longer than the cover foil 11 and detection element 10 together so that usually an uncovered gap of a few millimeters in width usually remains from which air can escape when the capillary-active zone is filled with sample liquid. This gap also remains uncovered by the protective foil 12 so that its function remains ensured.

Example 1

Production of an analytical test element by the process according to the invention A double-sided adhesive tape with a thickness of 100 μm is glued as a spacer layer onto a 350 μm thick foil of polyethylene terephthalate MELINEX®, ICI, Frankfurt am Main, Germany). The carrier layer has a length of 25 mm and is 5 mm wide. A central notch-shaped recess of 1 mm width and 2 mm length is located on one of the short sides of the carrier layer as also described for example in the German Patent Application No. P 197 53 850.9. The contour for a cut-out of 2 mm width and 16 mm length which defines the geometry of the capillary channel is introduced through the adhesive tape laminated onto the carrier layer with the aid of an appropriately shaped cutting tool without the carrier layer being cut so deeply that its rigidity and stability would suffer. The length of the cut-out has to be selected to be slightly larger than the desired length of the capillary-active channel which is determined by its covering in order to ensure venting of the channel during filling with sample liquid. The non-required parts of the adhesive tape are pulled off the carrier layer immediately after introducing the contour. A 3 mm long and 5 mm wide detection film is glued onto the side of the remaining adhesive tape which provides the venting at a distance of 1 mm from the end of the cut-out A film is used as the detection film as is known from the German Patent Application No. P 196 29 656.0. The detection film is specific for the detection of glucose. A 12 mm long and 5 mm wide cover foil is glued onto the region of the adhesive tape that is still open between the notch-shaped recess and detection film so that the cover layer and detection film abut one another. The cover foil is composed of a 150 μm thick polyethylene terephthalate foil provided on one side with adhesive onto which a 6 μm thick polyethylene terephthalate foil (both: HOSTAPHAN®, Hoechst, Frankfurt am Main, Germany) coated with a 30 nm thick oxidized aluminium layer is glued on the side facing the capillary channel. In this case the thinner foil extends ca. 500 μm beyond the thicker foil on the side facing the detection film. When the cover layer is mounted on the adhesive tape care must be taken that the protruding end of the thinner foil comes to lie between the detection element and the thicker foil of the cover foil. In order to cover areas of the adhesive tape that are still exposed, these are covered with a 175 μm thick MELINEX® foil without, however, covering functional areas.

The test element obtained in this manner has a capillary channel of 15 mm length, 2 mm width and 0.1 mm height. The channel can take up 3 μl sample liquid. An area of 3 mm ×2 mm of the detection film is wetted by the sample.

What is claimed is:

1. A process for the production of a analytical device with a capillary-active zone in which
   (a) a carrier layer is provided;
   (b) a spacer layer is laminated onto the carrier layer;
   (c) a contour which determines the shape of the capillary-active zone is cut through the spacer layer;
   (d) those parts of the spacer layer which are not required for shaping the capillary-active zone are removed from the carrier layer; and
   (e) a cover layer is mounted on the spacer layer so that the capillary-active zone and the devices are formed.

2. The process as claimed in claim 1 wherein the spacer layer comprises a double-sided adhesive tape.

3. The process as claimed in claim 1 wherein the cover layer comprises a plurality of parts.

4. The process as claimed in claim 1 wherein the cover layer comprises an analytical detection film.

5. The process as claimed in claim 1 wherein the analytical device is an analytical test element.

6. The process as claimed in claim 1 wherein the spacer layer is laminated onto the carrier layer immediately before cutting the contour of the capillary-active zone.

7. The process as claimed in claim 1 wherein those parts of the spacer layer that are not required to form the capillary-active zone are removed immediately after cutting the contour of the capillary-active zone.

8. The process as claimed in claim 1 wherein the carrier layer, the spacer layer and the cover layer comprise tape materials.

9. The process as claimed in claim 8 wherein the contour is formed as a continuous cut by a rotary cutting tool.

10. The process as claimed in claim 9 wherein the rotary cutting tool utilized comprises a cutting roller and a counterpressure cylinder.

11. The process as claimed in claim 8 wherein analytical devices are produced and the analytical devices are separated by cutting after applying the cover layer.

12. A process for the production of an analytical device with a capillary active-zone in which (a) a carrier layer is provided;

(b) a spacer layer is laminated onto the carrier layer;

(c) a contour which determines the shape of the capillary-active zone is punched through the spacer layer;

(d) those parts of the spacer layer which are not required for shaping the capillary-active zone are removed from the carrier layer; and (e) a cover layer is mounted on the spacer layer so that the capillary-active zone and the devices are formed.

13. The process as claimed in claim 12 wherein the spacer layer comprises a double-sided adhesive tape.

14. The process as claimed in claim 12 wherein the cover layer comprises a plurality of parts.

15. The process as claimed in claim 12 wherein the cover layer comprises an analytical detection film.

16. The process as claimed in claim 12 wherein the analytical device is an analytical test element.

17. The process as claimed in claim 12 wherein the spacer layer is laminated onto the carrier layer immediately before punching the contour of the capillary-active zone.

18. The process as claimed in claim 12 wherein those parts of the spacer layer that are not required to form the capillary-active zone are removed immediately after punching the contour of the capillary-active zone.

19. The process as claimed in claim 12 wherein the carrier layer, the spacer layer and the cover layer comprise tape materials.

20. The process as claimed in claim 19 wherein the contour is formed as a continuous cut by a rotary cutting tool.

21. The process as claimed in claim 20 wherein the rotary cutting tool utilized comprises a cutting roller and a counterpressure cylinder.

22. The process as claimed in claim 19 wherein analytical devices are produced and the analytical devices are separated by punching after applying the cover layer.

\* \* \* \* \*